United States Patent [19]

Yanaihara et al.

[11] 3,953,418

[45] Apr. 27, 1976

[54] NOVEL HUMAN PROINSULIN C-PEPTIDE DERIVATIVES

[75] Inventors: Noboru Yanaihara, Shizuoka; Osamu Ikeda, Tokyo, both of Japan

[73] Assignee: Daiichi Radioisotope Laboratories, Ltd., Tokyo, Japan

[22] Filed: July 15, 1974

[21] Appl. No.: 488,855

[30] Foreign Application Priority Data

July 14, 1973 Japan.............................. 48-79469

[52] U.S. Cl............................... 260/112.7; 424/12; 424/178
[51] Int. Cl.².................. C07C 103/52; A61K 37/26
[58] Field of Search...................... 260/112.7, 112.5

[56] References Cited
UNITED STATES PATENTS
3,715,434   2/1973   Mende............................ 260/112.5

OTHER PUBLICATIONS
Dreier et al: Chem. Abstr., 75:95273b (1971).
Glover et al: Chem. Abstr., 66:72443g (1967).
Ko et al: Eur. J. Biochem., 20, 190–199, (1971); cited in Chem. Abstr., 75:30159z.
Yanaihara et al: Chem. Pharm. Bull., 18, 417–420, (1970); cited in Chem. Abstr., 72:90858z.

*Primary Examiner*—Lewis Gotts
*Assistant Examiner*—Reginald J. Suyat
*Attorney, Agent, or Firm*—Sughrue, Rothwell, Mion, Zinn & Macpeak

[57] ABSTRACT

A peptide having an amino acid sequence of Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg; Tyr-Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg; or Tyr-Arg-Arg-Glu-Ala-Glu-Asp-Leu-Gln-Val-Gly-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg; and the N formyl-Lys derivative thereof.

6 Claims, 3 Drawing Figures

X = NHNHBoc

NOVEL HUMAN PROINSULIN C-PEPTIDE DERIVATIVES

BACKGROUND OF THE INVENTION

1. Field of the Invention

The present invetion relates to novel human C-peptide derivatives, and, more particularly, relates to tyrosylated human C-peptide derivatives and radioactive iodized derivatives thereof. These C-peptide derivatives are useful for the radioimmunoassay of human C-peptide or proinsulin in serum.

2. Description of the Prior Art

Human proinsulin, which is a precursor of insulin, is known to have the structure as $NH_2$-(B-chain of insulin)-Arg-Arg-(C-peptide)-Lys-Arg-(A-chain) (Proc. Nat. Acad. Sci., Vol. 67, pages 148 to 155 (1970)). As the blood level of human C-peptide is relative to those of proinsulin and insulin, quantitative analysis of C-peptide, especially by a radioimmunoassay method, is of great importance in clinical analysis.

Steiner at al reported that human C-peptide is extracted from human pancreas and also proposed its amino acid sequence as Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln, (J. Biol. Chem., Vol. 246, pages 1375 to 1386 (1971)).

Further, Steiner et al reported the immunoassay method using $^{131}I$-tyrosylated C-peptide which is prepared from the extracted C-peptide (Diabetes, Vol. 19, pages 546 to 551, and Proc. Nat. Acad. Sci., Vol. 67, pages 148).

In the process of immunoassay, antiserum containing antibody to human C-peptide is necessary and the antiserum is generally produced in animals such as guinea pigs or rabbits with antigen, i.e., C-peptide. Usually, the antiserum is required to have an adequate antibody unit so high as being measurable even after high dilution, desirably 3,000 to 5,000 times dilution, in order to avoid the undesirable effect of various kinds of inevitable contaminants in the serum.

The antiserum given from C-peptide in Steiner's report enables measurement with 1,000 times dilution, however, this is not yet satisfactory. Moreover, the extraction of C-peptide from human pancreas can not be carried out on a large scale, and C-peptide is not obtained in high yield by a synthetic procedure because it is slightly soluble in an aqueous buffer solution.

SUMMARY OF THE INVENTION

The object of this invention is to provide novel C-peptide derivatives useful for the immunoassay of human C-peptide in serum. The C-peptide as described above has 31 amino acids in its sequence and is called Steiner's C-peptide, human proinsulin$_{33-63}$ or C-peptide (31) in this specification, while this invention relates to novel derivatives of the C-peptide (31) represented by Arg-Arg-Steiner's C-peptide-Lys-Arg which is called human proinsulin$_{31-65}$ or C-peptide (35). The present invention further includes the two derivaties such as tyrosylated C-peptide (35) and a radioiodized compound thereof, which is useful for immunoassay methods. Of course, they include minor modified derivatives such as the N -formyl-Lys and the like.

Figure 1:
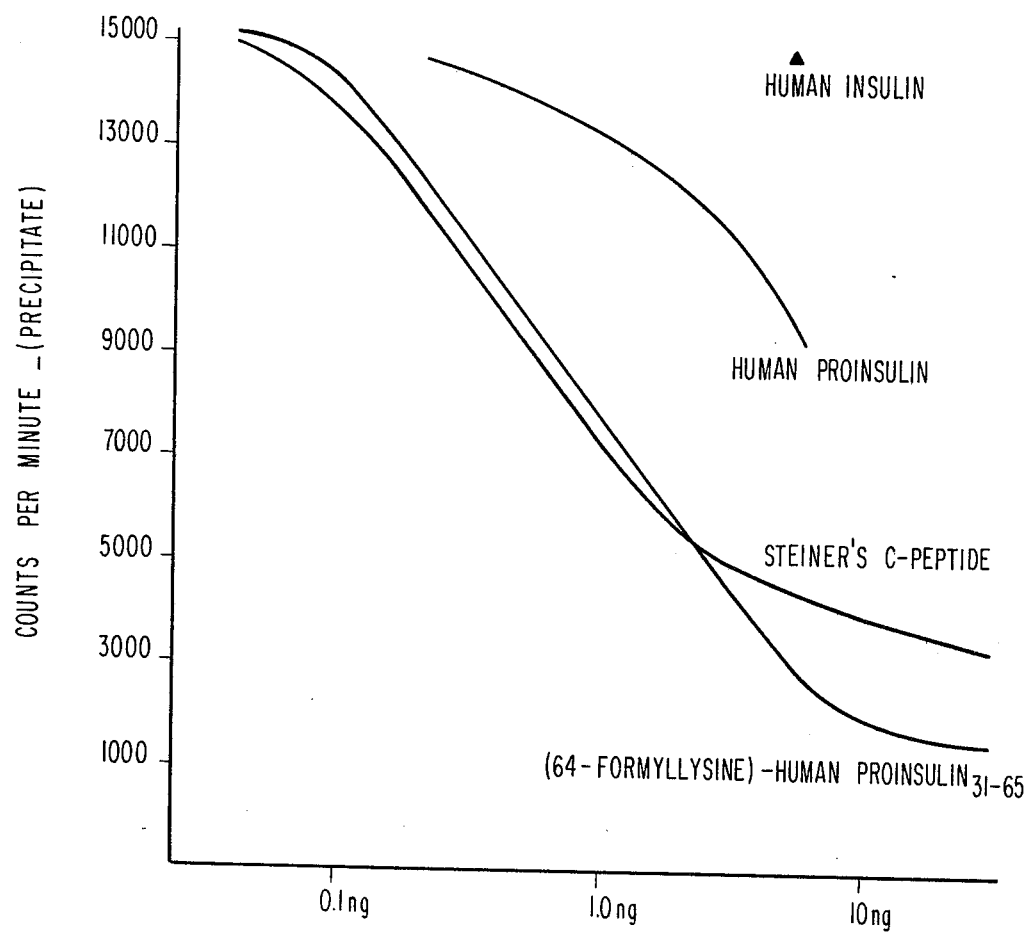
FIG. 1 shows the dose response curve of synthetic [64-formyllysine]-human proinsulin$_{31-65}$ and Steiner's C-peptide using $^{125}I$-tyrosylated[64-formyllysine]-human proinsulin$_{31-65}$ obtained by this invention. Both response curve are coincident with each other.
Figure 2:
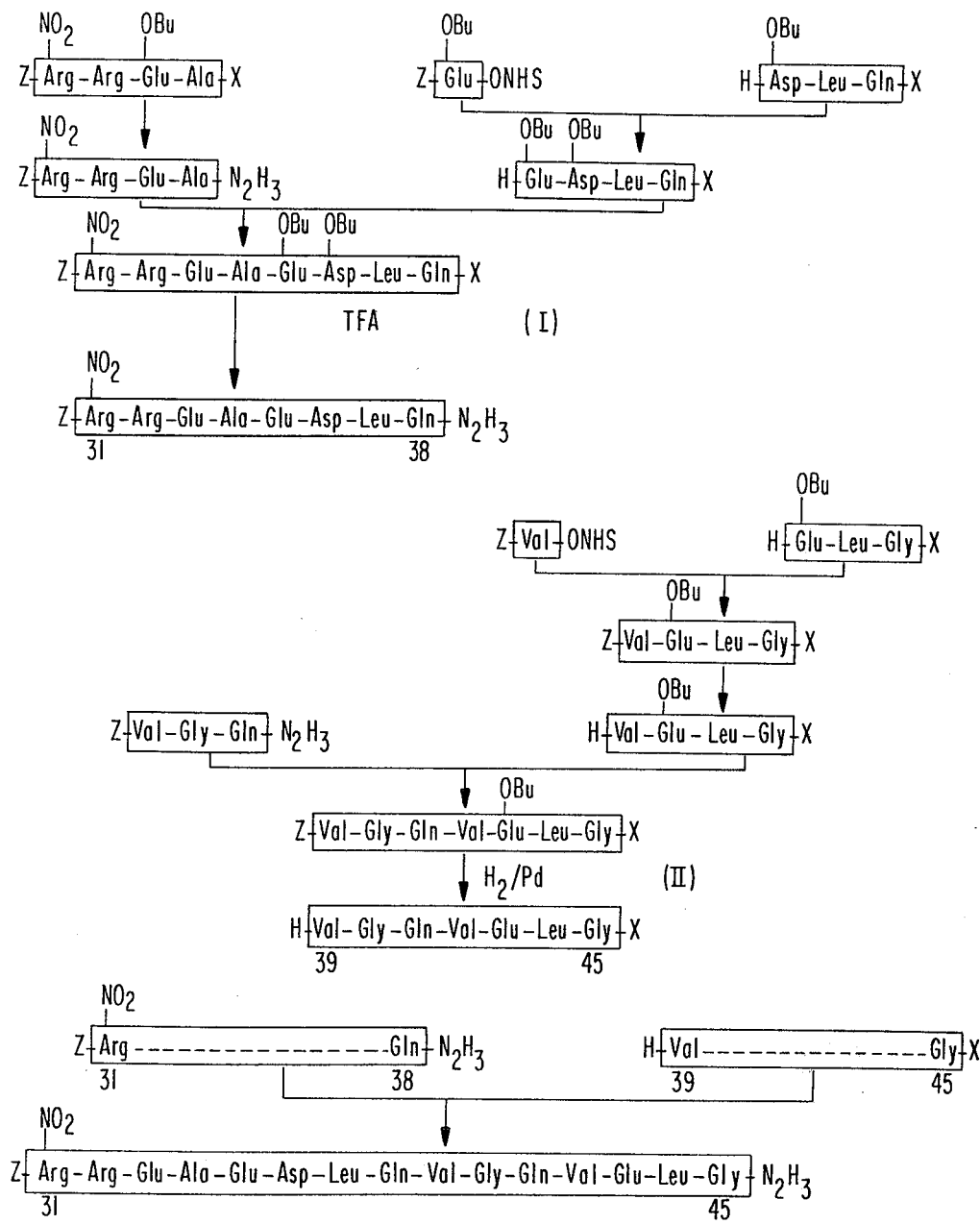
FIGS. 2 and 3 show the preparations of peptides of this invention.
Figure 3:
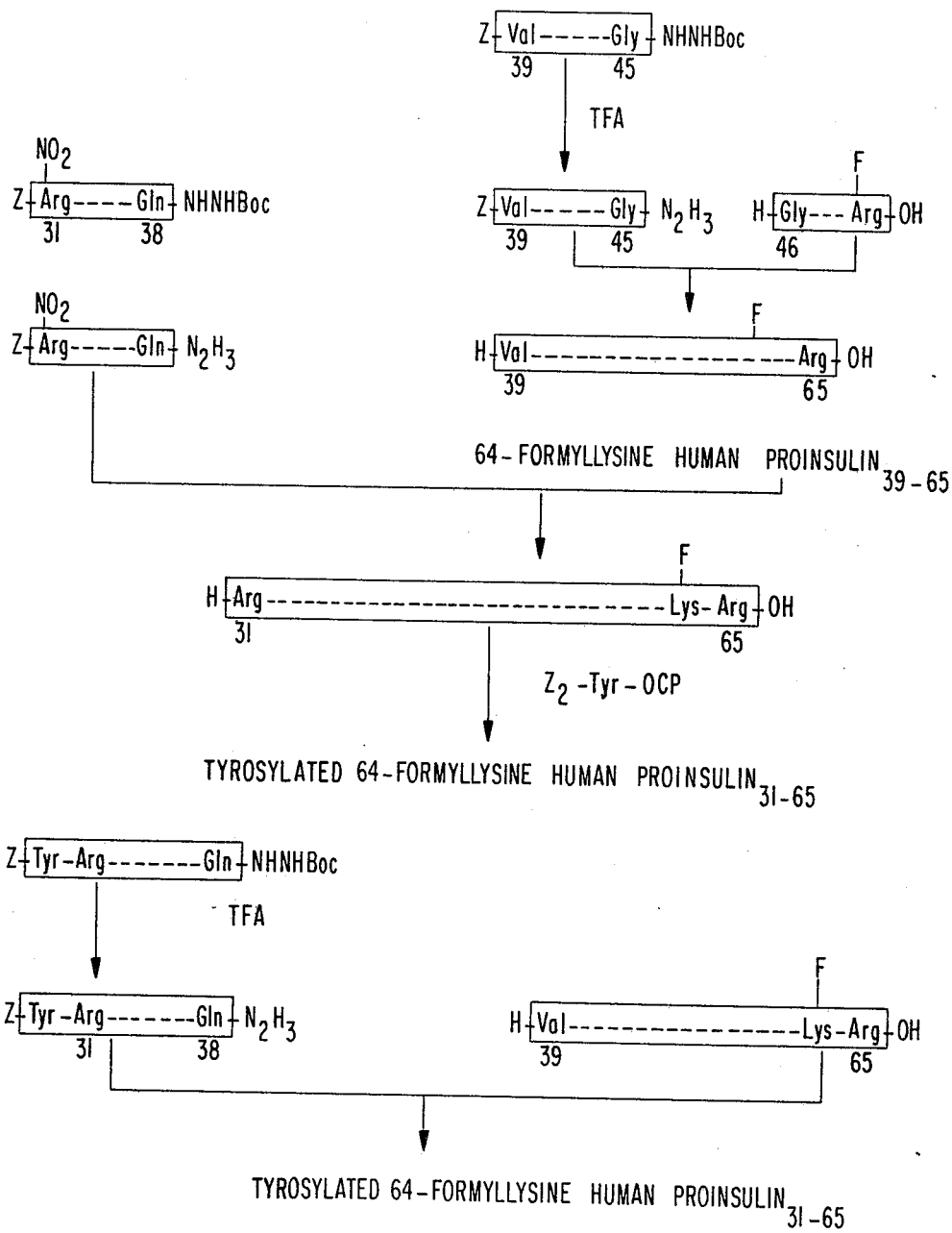

In the reaction schemata, "ONHS" stands for "N-hydroxysuccinimide ester".

DETAILED DESCRIPTION OF THE INVENTION

This invention will be explained by the following preferred embodiments.

C-peptide (35) is made to react with tyrosine, or a partial pedtide of C-peptide (35) is made to react with a tyrosylated peptide which is a counterpart of the partial peptide. An amino group of tyrosine or a tyrosine part of the peptide is desirable to be protected by a suitable protective group known in the peptide synthesis such as benzyloxycarbonyl (Z), tertiarybutyloxycarbonyl (Boc) and the like. Tyrosine or the tyrosylated counterpart of C-peptide (35) can be used in the reaction as an activated ester, and any activated ester known in the peptide synthesis can be used. Examples of such an ester are trichlorophenyl ester, p-nitrophenyl ester, pentachlorophenyl ester and the like.

The reaction is carrried out, for example, between one mole of the former reactant and about 2 to 10 moles of the latter reactant (an activated tyrosine ester or an activated ester having the tyrosine residue at the N-terminal) in a solvent with a pH of about 7 to 9 which is inactive to the reactants, at about $-15°C$ to $+20°C$ for about 0.5 to 48 hours.

The resulting tyrosylated C-peptide (35) having protective groups can be reduced in a hydrogen stream in the presence of a catalyst such as palladium-black, or be treated with an acid such as trifluoroacetic acid or hydrochloric acid to give tyrosylated C-peptide (35). However, the protective group such as a formyl group at an $\epsilon$-amino group of the penultimate lysine residue (position 64) need not be removed, when the group does not disturb immunoreactivity. The tyrosylated C-peptide (35) can be purified by a conventional method such as gel-filtration with Sephadex G-50, Bio-Gel P-6 and the like.

In order to iodize the tyrosylated C-peptide (35) with radioactive iodine, it is very convenient to carry out the method of Hunter and Greenwood (Nature, Vol. 194, pages 494 to 497 (1962)). In this method, the tyrosylated C-peptide (35) is dissolved in water and made to react with radioactive sodium iodide such as $Na^{125}I$ or $Na^{131}I$ and chroramine T as an oxidizing agent for approximate 30 seconds. The reaction is then stopped by the addition of sodium metabisulfite. As for the radioactive iodine, $^{125}I$ or $^{131}I$ is preferable. When the purification is performed by gel-filtration and the like, the obtained substance has rodioactive iodine on the tyrosine phenyl group.

All amino acids used in this invention are in the optically active L-form except for glycine, and they are, in general, represented by the initial 3 letters of the parent amino acids, a glutaminyl group is represented by "Gln".

C-peptide (35) and its radioiodized tyrosylated derivative are very useful for immunoassay procedures, and the antibody produced by C-peptide (35) can be used at about 10,000 times dilution, so this invention provides very useful materials.

The following examples illustrate this invention in greater detail.

The peptides used as the starting materials in Examples 1 and 2 are prepared by the segmentation method shown in the following schema and examples. In this specification, peptides are occasionally represented, for convenience sake, by abbreviated forms in which the two terminal amino acids (N-terminal and C-terminal) are shown with the number being used in human proinsulin.

EXAMPLE A

Synthesis of
Z-Tyr-Arg($H^+$)-Arg($H^+$)-Glu-Ala-Glu(oBu)-Asp(oBu)-Leu-Gln-NHNH-Boc Leu-Gln-NHNH-Boc Z-Arg($NO_2$)-Arg($H^+$)-Glu-Ala-Glu(oBu)-Asp(oBu)-Leu-Gin-NHNHBoc [m.p. 175° to 176°C(dec), $Rf^I$ 0.62, $Rf^{II}$ 0.75, amino acid ratios in acid hydrolysate : Arg + Orn 2.08 Asp 0.99 Glu 2.97 Ala 1.01 Leu 0.97; Anal Calcd. for $C_{61}H_{100}N_{18}O_{21}$·acetate dihydrate] (519 mg) was hydrogenated over Pd in Me-OH(20 ml) and 10% acetic acid (5 ml) for 20 hours. The catalyst was removed by filtration, the solvent was evaporated and the residue was lyophilized.

Z-Tyr-OCP was added to a solution of the above hydrogenated material in dimethylformamide (10 ml) and the mixture was kept at room temperature for 20 hours. The solvent was concentrated and ethylacetate was added. The resulting solid was collected, dried and washed with ethylacetate and $H_2O$. Yield 240 mg, m.p. 188° to 189°C(dec), $Rf^I$ 0.51, Anal. Calcd. for $C_{70}H_{110}N_{18}O_{21}$. diacetate dihydrate: C, 52.4 : H, 7.3 : N, 14.9, Found: C, 52.4 : H, 6.9 : N, 14.7.

EXAMPLE B

Synthesis of Tyrosylated [64-Formyllysine]-human proinsulin$_{31-65}$

Z-Tyr-Arg-Arg-Glu-Ala-Glu(oBu)-Asp(oBu)-Leu-Gln-NHNHBoc (195 mg) in trifluoroacetic acid 1.0 ml was allowed to stand at room temperature (e.g., 20° to 30°C) for 1 hour and anhydrous ether was added. The resulting hydrazide was collected by filtration, washed with ether and dried over KOH in vacuo. The hydrazide was dissolved in dimethylformamide (5 ml) and 6N HCl in dioxane (0.09 ml). The solution was cooled to −15°C and 10% isoamylnitrite in dimethylformamide (0.14 ml) was added. After 3 minutes, the resulting azide solution was adjusted to a pH of 7.5 by the addition of triethylamine and added to the solution of the above [64-formyllysine]-proinsuline$_{39-65}$ (48 mg) in dimethylformamide (5 ml) and hexamethyl phosphorotriamide (1 ml) at −10°C. The mixture was stirred at 4°C for 24 hours and the solvent was evaporated. The residue was treated in the manner described for the preparation of [64-formyl-lysine]-proinsulin$_{39-65}$. The mixture of the products was hydrogenated over Pd in 50% acetic acid (30 ml) for 20 hours. The catalyst was removed by filtration and the solvent was evaporated in vacuo.

The residue was dissolved in 1M acetic acid (5 ml) and the solution was applied to the column of Bio-Gel P-6 (2.5 × 120 cm). Individual fractions (8 ml each) were collected.

Fractions No.27-50 was pooled and the solvent was concentrated. The residue was lyopilized. This material was further purified by CM Sephadex column chromatography. The lyophilized material dissolved in water (300 ml) was applied to the CM Sephadex C-25 column (2.5 × 4 cm), which was washed with water (200 ml) and eluted with 0.02M ammonium acetate (400 ml).

Individual fractions (10 g each) were collected and location of the peptide was detacted by Sakaguchi and Chlorine tests. The eluates containing desired material was pooled, the solvent was evaporated in vacuo, and the residue was lyophilized from small volumes of water and desalted by Bio Gel P6; yield 41 mg. $[\alpha]_D^{24}$ −97.9° (C 0.21, 10% acetic acid); $Rf^I$ 0.12, $Rf^{II}$ 0.37, amino acid ratios in acid hydrolysate: Asp 0.97 Ser 1.60 Glu 8.13 Pro 1.94 Gly 7.15 Ala 3.08 Val 2.05 Leu 5.96 Tyr 0.92 Lys 0.95 Arg 2.85 $NH_3$ 4.41 (recovery 90%)

EXAMPLE C

Z-Tyr-Arg-Arg-Glu-Ala-Glu-Asp-Leu-Gln-Val-Gly-Gln-Val-Glu-Leu-Gly.NHNH

Z-Val-Gly-Gln-Val-Glu(oBu)-Leu-Gly-NHNHBoc(101 mg) was hydrogenated over Pd in methanol (5 ml), 1-butanol (5ml) and 10% acetic acid (3 ml) for 20 hours. The catalyst was removed, the solvent was evaporated and the residue was dried $Rf^I$ 0.48.

Z-Tyr-Arg-Arg-Glu-Ala-Glu(oBu)-Asp-(oBu)-Leu-Gln-NHNHBoc (182 mg) was treated with trifluoro acetic acid (0.5 ml) at room temperature (e.g., 20° to 30°C) for 50 minutes and anydrous ether was added. The resulting precipitate ($Rf^I$ 0.18) was collected by filtration and dried.

This hydrazide was dissolved in dimethyl formamide(6 ml) and 6N HCl in dioxane (0.15 ml). The solution was cooled at −10°C and 10% isoamylnitrite in dimethylformamide (0.16 ml) was added.

The solution was adjusted to a pH of 7.5 by the addition of triethylamine.

This azide solution was combined with a solution of the above hydrogenated material in dimethylformaide (5 ml) at −10°C. The mixture was stirred at 4°C for 44 hours and condensed to a small volume.

AcO-Et was added to give a solid which was collected and dried. The solid was dissolved in trifluoro acetic acid (1 ml) and the solution was kept at room temperature (e.g., 20° to 30°C) for 40 minutes. Anhydrous ether was added to give a solid, which was collected and dried. The ensuing hydrazide was dissolved in 50% acetic acid (16 ml) and the solution was purified by gel filtration on Bio-Gel-P6 (2.5 × 120 cm), Yield 130 mg, $Rf^I$ 0.26 $Rf^{II}$ 0.64, amino acid ratios in acid hydrolysate. Asp 1.31 Glu 5.22 Gly 1.87 Ala 1.05 Val 1.97 Leu 1.99 Tyr 0.97 Arg 2.03 (recovery 89%)

EXAMPLE D

Tyrosylated [64-Formyllysine]-Human Proinsulin$_{31-65}$.

The above Z-Tyr-Arg($H^+$)-Arg($H^+$)-Glu-Ala-Glu-Asp-Leu-Gln-Val-Gly-Gln-Val-Glu-Leu-Gly-$NHNH_2$ (60 mg) was dissolved in dimethylformamide (15 ml) and 6N HCl in dioxane (0.30 ml). The solution was then cooled at −10°C and 10% isoamylnitrite (0.04 ml) was added. The solution was adjusted to a pH of 7.5 by the addition of triethylamine.

The resulting azide solution was added to the solution of H-Gly-Gly-Pro-Gly-Ala-Gly-Ser-Leu-Gln-Pro-Leu-Ala-Leu-Glu-Gly-Ser-Leu-Gln-Lys(F)-Arg($H^+$)OH

[Rf' 0.14, Rf'' 0.46, $[\alpha]_D^{29}$ −92.7°(C 0.74, 10% acetic acid)]; amino acid ratios in acid hydrolysate: Ser 1.76 Glu 3.09 Pro 1.90 Gly 4.90 Ala 2.14 Leu 3.92 Lys 1.02 Arg 1.01,[Anal. Calcd. for $C_{84}H_{142}N_{26}O_{28}$ diacetate tetrahydrate: C 49.3 : H 7.4 : N 17.4. Found: C 49.5 : H 7.5 : N 16.9 ] (30 mg) in dimethylformamide 10 ml at −10°C.

The solution was stirred at 4°C for 48 hours and the solvent was evaporated. The residue was precipitated by the addition of ether and dried.

This was hydrogenated over Pd in 50% acetic acid (30 ml) for 24 hours. The catalyst was removed and the solvent was evaporated.

The hydrogenated material was purified in the manner described for the preparation of [64-formyllysine]-human proinsulin$_{31-65}$. Yield 39 mg, Rf' 0.12, Rf'' 0.37, $[\alpha]_D^{27}$ −97.7° (C 0.1 in 10% acetic acid); amino acid ratios in acid hydrolysate; Asp 1.04 Ser 1.78 Glu 7.88 Pro 2.05 Gly 6.84 Ala 3.07 Val 2.06 Leu 6.04 Tyr 1.00 Lys 0.98 Arg 3.03 NH$_3$ 4.89 (recovery 85%)

EXAMPLE E

[64-Formyllysine]-Human Proinsulin$_{31-65}$ Acetate Hydrate

Z-Arg(NO$_2$)Arg-Glu-Ala-Glu(OBu)-Asp(OBu)-Leu-Gln-NHNH-Boc [mp 175° to 176°C (dec)] (488 mg) in trifluoroacetic acid (5 ml) was allowed to stand at room temperature (e.g., 20° to 30°C) for 1 hour and anhydrous ether was added. The resulting hydrazide was collected by filtration, washed with ether and dried over KOH in vacuo. The hydrazide was dissolved in dimethylformamide (10 ml) and 6N HCl in dioxane (0.17 ml). The solution was cooled at −15°C and 10% isoamylnitrite in dimethylformamide (0.35 ml) was added. After 3 minutes, the resulting azide solution was adjusted to a pH of 7.5 by the addition of triethylamine and then was added to the solution of [64-formyl-lysine]-proinsulin$_{39-65}$ (120 mg) in dimethylformamide (10 ml) and hexamethylphosphorotiamide (2 ml) at −10°C.

The mixture was stirred at 4°C for 24 hours and the solvent was evaporated. The residue was treated in the same manner described for the procedure of [64-formyllysine]-proinsuline$_{39-65}$. The mixture of the products was hydrogenated over Pd in 50% acetic acid (50 ml) for 48 hours. The catalyst was removed by filtration and the solvent was evaporated in vacuo. The residue was dissolved in 50% acetic acid (5 ml) and the solution was applied to the column of Bio-Gel-P-6 (3.0 × 180 cm). Individual fractions (10 g each) was collected. Fractions No.32–50 were pooled and the solvent was concentrated. The residue was lyophilized. This material was further purified by CM Sephadex column chromatography. The lyophilized material dissolved in water (300 ml) was applied to the CM-Sephadex C-25 column (2.5 × 5 cm), which was washed with water (200 ml) and eluted with 0.02M ammonium acetate (500 ml). Individual fractions (10 g each) were collected and location of the peptide was detected by Sakaguchi and chlorine tests. The eluates containing desired material was pooled. The solvent was evaporated in vacuo, and the residue was lyophilized with a small volume of water and desalted by Bio-Gel P-6. Yield 150 mg; $[\alpha]_D^{29}$ −96.8° (C 0.58,10% acetic acid), Rf' 0.11, Rf'' 0.35, amino ratios in acid hydrolysate; Asp 1.04, Ser 1.78, Glu 7.88, Pro 2.05, Gly 6.84, Ala 3.07, Val 2.06, Leu 6.04, Lys 0.98, Arg 3.03 NH$_3$ 4.28 (recovering 91%).

EXAMPLE F

H-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys(F)-Leu-Gln-Lys(F)- Acetate Hydrate ([64-Formyllysine]-human proinsulin$_{39-65}$)

Z-Val-Gly-Gln-Val-Glu(OBu)-Leu-Gly-NHNH-Boc[mp 253°–254°C (decomp.)], Rf' 0.77, Rf'' 0.85, $[\alpha]_D^{26}$ −32.1° (C 1.0 in DMF), Amino acid ratios in acid hydrolysate Glu$_{2.02}$ Gly$_{2.03}$ Val$_{1.98}$ Leu$_{0.96}$; Anal. Calcd. for $C_{47}H_{76}N_{10}O_{14}$: C, 56.2; H, 7.6; N, 13.9: Found C, 55.9; H, 7.5; N, 14.0 (603 mg) in trifluoroacetic acid (10 ml) was allowed to stand at room temperature (e.g., 20° to 30°C) for 1 hour and anhydrous ether was added. The resulting hydrazide was collected by filtration, washed with ether and dried over KOH in vacuo. The hydrazide was dissolved in dimethylformamide (10 ml) and 6N HCl in dioxane (0.30 ml), and the solution was cooled to −15°C and 10% isoamylnitrite in dimethylformamide (0.82 ml) was added. After 3 minutes, the reaction mixture was adjusted to a pH of 7.5 by the addition of triethylamine and then added to a solution of H-Gly-Gly-Pro-Gly-Ala-Gly-Ser-Leu-Gln-Pro-Leu-Ala-Leu-Glu-Gly-Ser-Leu-Gln-Lys(F)-Arg(H$^+$)−OH (248 mg) [Rf' 0.14, Rf'' 0.46, $[\alpha]_D^{29}$ −92.7° (C 0.74 in 10% AcOH), Anal. Calcd, for $C_{84}H_{142}N_{26}O_{28}$·2CH$_3$COOH. 4H$_2$O: C, 49.3; H, 7.4; N, 17.4. Found: C, 49.5; H, 7.5; N, 16.9. Amino acid ratios in acid hydrolysate Ser$_{1.76}$ Glu$_{3.09}$ Pro$_{1.90}$ Gly$_{4.90}$ Ala$_{2.14}$ Leu$_{3.92}$ Lys$_{1.02}$ Arg$_{1.01}$] in dimethylformamide (10 ml), hexamethylphosphoric triamide (6 ml) and triethylamine (0.06 ml) at −10°C. The mixture was stirred at 4°C for 24 hours and the solvent was evaporated. The residue dissolved in 1-BuOH was washed six times with 2% acetic acid (equilibrated with 1-BuOH): The 1-BuOH layers were combined and evaporated. The residue was solidified by the addition of ether and the solid was collected by filtration and dried.

The mixture of the products was hydrogenated over Pd in 50% acetic acid (50 ml) for 20 hours. The catalyst was removed by filtration and the solvent was evaporated in vacuo. The residue was dissolved in 50% acetic acid (10 ml) and the solution was applied to a column of Bio-Gel P-6 (100-200 mesh) (4.0 × 120 cm). Individual fractions (15 g each) were collected. Location of the peptide was detected by chlorine-tolidine test on TLC. Fractions No. 26 to 39 were pooled and the solvent was evaporated. The residue was lyophilized with a small volume of water. Yield 251 mg, $[\alpha]_D^{24}$ −87.6° (C 0.25 in 10% acetic acid), Rf' 0.20, Rf'' 0.55. Amino acid ratios in acid hydrolysate Ser$_{1.78}$ Glu$_{5.04}$ Pro$_{1.95}$ Gly $_{7.08}$ Ala$_{1.92}$ Val$_{2.07}$ Leu$_{4.99}$ Lys$_{0.98}$ Arg$_{0.97}$ NH$_{33.48}$ (Recovery 82%).

EXAMPLE 1

34 mg of Z-Tyr-Arg-Arg-Glu-Ala-Glu-Asp-Leu-Gln-Val-Gly-Gln-Val-Glu-Leu-Gly-NH.NH$_2$ was dissolved in a mixture of 6 mg of dimethylformamide and 0.1 ml of 6N HCl dioxane solution and after cooling to −15°C, 0.03 ml of dimethylformamide containing 10% w/v isoamyl nitrite was added. After one minute, the resulting solution was neutralized with triethylamine, and then was added to a solution of 30 mg of H-Gly-Gly-Pro-Gly-Ala-Gly-Ser-Leu-Gln-Pro-Leu-Ala-Leu-Glu- Gly-Ser-Leu-Gln-Lys(F)-Arg-OH.acetate dissolved in 5.0 ml of dimethylformamide at −10°C.

This combined solution was stirred at 4°C for 48 hours, and the solvent was removed. The residue was washed with ethylether and dried, to give crude tyrosylated C-peptide (35) with protective groups. This peptide was added to 40 ml of 50% acetic acid solution and the mixture was stirred for 48 hours in a hydrogen stream in the presence of palladium black at room temperature (e.g., 20° to 30°C). Then, the reaction mixture was filtered and the solvent was removed. The residue was then dried. When this residue was gel-filtered with Sephadex G-50 column (2.5×80 cm), 23 mg of pure tyrosylated C-peptide (35), H-Try-Arg-Glu-Ala-Glu-Asp-Leu-Gln-Val-Gly-Gln-Val-Glu-Leu-Gly-Gly-Pro-Gly-Ala-Gly-Ser-Leu-Gln-Pro-Leu-Ala-Leu-Glu-Gly-Ser-Leu-Gln-Lys-(F)-Arg-OH(tyrosylated [64-formyllysine]-human proinsuline$_{31-65}$) was obtained. $[\alpha]_D^{24}$ −97.9° (C 0.21, 10% acetic acid)

Thin layer chromatography:
Rf 0.11 (Silica-gel, 1-butanol: acetic acid: water = 4:1:5) Rf 0.35 (Silica-gel, pyridine: acetic acid water : 1-butanol = 20:6:24:30)

Amino acid analysis (6N HCl, 100°C 24 hours.):

The mole ratio of each amino acid is found to fall in the theoretically identical range. The value found is as follows: Asp 1.05, Ser 1.60, Glu 7.90, Pro 2.07, Gly 6.98, Ala 2.92, Val 1.96, Leu 6.10, Tyr 0.93, Lys 1.10, Arg 2.98.

EXAMPLE 2

To the solution of 15 mg of H-Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys(F)-Arg-OH, 7 ml of dimethylformamide, 0.7 ml of distilled water and 0.1 ml of triethylamine, were added 10 mg of (Z)$_2$-Tyr.trichlorophenyl ester and the mixture was stirred at 20°C for 40 hours. After removing the solvent, the residue was washed with ethyl ether and dried. The residue was dissolved in 20 ml of 50% acetic acid and the mixture was stirred for 48 hours in the presence of palladium black, and 13 mg of crude tyrosylated C-peptide (35) having a formyl group at lysine part was obtained. This was dissolved in one ml of 50% acetic acid, and the solution was gel-filtered with the Sephadex G-50 column$_{(2.5 \times 80cm)}$ to give purified tyrosylated [64-formyllysine]-human proinsuline$_{31-65}$. The characteristics of this product were almost equal with that obtained in Example 1.

EXAMPLE 3

In 1 ml of water, 500 µg of tyrosylated human C-peptide was dissolved and 3 µl of the solution was iodized with 2 mCi of $^{125}$I according to the method of Hunter and Greenwood. The resulting $^{125}$I-tyrosylated [64-formyllysine]-human proinsuline$_{31-65}$ was gel-filtered with the Bio-Gel P 30 column (50 × 1 cm) using 3M acetic acid as eluant. The radio-activity of each fraction was counted and several fractions indicating the peak of the activity were collected. The fractions were combined and used for the radioimmunoassay. About 100 mCi/mg of the radioactivity was observed.

IMMUNOASSAY

To determine C-peptide in serum utilizing the radioactive iodized tyrosylated C-peptide (35), the following method was carried out. First, 1.0 mg of human C-peptide (35) was dissolved in 1.0 ml of 0.9% NaCl solution, and then suspended into 1.0 ml of complete Freund's adjuvant. This agent was subcutaneously injected to four rabbits. Four weeks after injection, the second immunity was given in the same manner as above with 0.5 mg of C-peptide(35). Totally, three or four times of immunization were carried out. 10 days after the last injection, the blood was collected and then the antiserum was obtained. Into a test tube containing 0.5 ml of 0.05 M phosphate buffur (pH 7.5, containing 0.5% bovine serum albumin and 0.15 M sodium chloride) and 0.1 ml of 0.1 M EDTA aqueous solution, 0.1 ml of a diluted antiserum (1 : 10,000) of a synthetic C-peptide ([64-formyllysine]-human proinsulin$_{31-65}$) was added.

To this, 0.2 ml of patient serum and 0.1 ml of $^{125}$I-tyrosylated [64-formyllysine]-human proinsulin$_{31-65}$ aqueous solution were added successively. After mixing well, the mixture was incubated at 4°C for 48 hours.

To the resulting mixture, 0.1 ml of diluted normal rabbit serum and 0.1 ml of diluted goat antibody to rabbit γ-globulin were added. After mixing well, the mixture was incubated at 4°C for 24 hours. Then, it was centrifuged for 30 minutes at 3,000 rpm. After removing the supernatant, the radioactivity of the precipitate was determined using gamma-counter. The concentration of C-peptide in patient serum was read directly from the dose response curve constructed preliminary.

The dose response curve (standard curve) was constructed by the following procedure. Standard solutions of a synthetic C-peptide (for example, [64-formyllysine]-human proinsulin$_{31-65}$) was used instead of patient serum in the above procedure. The count (or percentage count) was plotted on the ordinate and the concentration of standard solution was plotted on the abscissa (logarithmic scale) of semilogarithmic section paper as shown in FIG. 1.

While the invention has been described in detail and with reference to specific embodiments thereof, it will be apparent to one skilled in the art that various changes and modifications can be made therein without departing from the spirit and scope thereof.

What is claimed is:

1. A peptide having the amino acid sequence of Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg and the N$^\epsilon$-formyl-Lys-derivative thereof.

2. A peptide having the amino acid sequence of Tyr-Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg and the N$^\epsilon$-formyl-Lys-derivative thereof.

3. A radioiodized peptide having the amino acid sequence of Tyr-Arg-Arg-Glu-Ala-Glu-Asp-Leu-Gln-Val-Gly-Gln-Val-Glu-Leu-Gly-Gly-Pro-Gly-Ala-Gly-Ser-Leu-Gln-Pro-Leu-Ala-Leu-Glu-Gly-Ser-Leu-Gln-Lys-Arg and the N$^\epsilon$-formyl-Lys-derivative thereof.

4. A radioiodized peptide of claim 3, wherein the radioactive iodine is $^{125}$I.

5. A method for preparing the preparing the peptide of claim 2, which comprises reacting a peptide having the amino acid sequence of Z-Tyr-Arg-Arg-Glu-Ala-Glu-Asp-Leu-Gln-Val-Gln-Val-Gly-Gln-Val-Glu-Leu-Gly with a peptide having the amino acid sequence of Gly-Gly-Pro-Gly-Ala-Gly-Ser-Leu-Gln-Pro-Leu-Ala-Leu-Glu-Gly-Ser-Leu-Gln-Lys-Arg-OH or the $N^\epsilon$-formyl-Lys-derivative thereof.

6. A method of preparing the peptide claimed in claim 2, which comprises reacting a peptide having the amino sequence:

Tyr-Arg-Arg-Glu-Ala-Glu-Asp-Leu-Gln with a peptide having the amino acid sequence:

Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg or the $N^\epsilon$-formyl-Lys-derivative thereof.

* * * * *